United States Patent [19]

Woods et al.

[11] Patent Number: 4,664,908

[45] Date of Patent: May 12, 1987

[54] NON-COMEDOGENIC COSMETIC EMOLLIENTS

[75] Inventors: William B. Woods, Garfield; Melvin Brauer, E. Brunswick; Francis Duneczky, Westfield; Dominic Simone, Lincroft, all of N.J.; John F. Cope, Brooklyn, N.Y.

[73] Assignee: CasChem, Inc., Bayonne, N.J.

[21] Appl. No.: 782,769

[22] Filed: Oct. 1, 1985

[51] Int. Cl.$^4$ .................................................. A61K 7/42
[52] U.S. Cl. ........................................ 424/59; 424/63; 424/64; 424/70; 514/844; 514/859
[58] Field of Search .................. 514/859, 844; 424/70, 424/59, 60, 64

[56] References Cited

FOREIGN PATENT DOCUMENTS 108739   8/1981   Japan ...................................... 424/59
57-93932 6/1982   Japan ...................................... 424/59

OTHER PUBLICATIONS

Chem. Abs., 1983, vol. 98, pp. 80 83y, Nisshin Oil–(Abstract of 93,932).
Chem. Abs. 1970, vol. 73, pp. 48491v, Jacobi.
Morris et al., J. Soc. Cosmetic Chem., 8/83, pp. 215-225.

*Primary Examiner*—Dale R. Ore
*Attorney, Agent, or Firm*—Pennie & Edmonds

[57] ABSTRACT

A method for imparting non-comedogenicity to a cosmetic composition which comprises incorporating into a cosmetic composition a predetermined amount of an ester of ricinoleic acid to act as an emollient, said ricinoleic acid ester having the formula

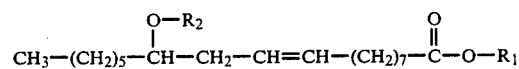

wherein:
$R_1$ is a straight or branched chain alkyl or alkenyl group having between one and 40 carbon atoms;
$R_2$ is hydrogen;

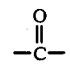

connected to a straight or branched chain alkyl or alkenyl group having between one and 40 carbon atoms; or between one and 40 moles ethylene or propylene oxide; and
the total molecular weight of $R_1$ and $R_2$ is at least about 150, preferably greater than about 170.

6 Claims, No Drawings

NON-COMEDOGENIC COSMETIC EMOLLIENTS

TECHNICAL FIELD

This invention relates to new and unique emollient additives for cosmetic compositions. More particularly, the invention relates to non-comedogenic ricinoleic acid esters for use as emulsifiers or emollients in such cosmetic formulations.

BACKGROUND OF THE INVENTION

Most cosmetic lotions and creams are emulsions of water-based and oil-based phases. An emulsion is a two-phase system consisting of two incompletely miscible liquids, the internal, or discontinuous, phase dispersed as finite globules in the other. Special designations have been devised for oil and water emulsions to indicate which is dispersed and which the continuous phase. Oil-in-water (o/w) emulsions have oil as the dispersed phase in water as the continuous phase. In water-in-oil (w/o) emulsions, water is dispersed in oil, which is the external continuous phase.

Emulsifiers or emollients are generally used to lower surface and interfacial tensions so as to increase the tendency of the emulsion to spread on a particular surface. The compounds also increase the stability of the formulation at particular pH ranges. Other uses for emollients include increasing the deposition of the emulsion onto a particular surface (i.e., such as skin or hair), or increasing the consistency or thickness of the overall product.

In the prior art, preferred emollients for such cosmetics include those compounds which impart the desired properties to the speciific cosmetic composition. An article by Morris et al. entitled "Use of Rabbit Ear Model in Evaluating the Comedogenic Potential of Cosmetic Ingredients," J. Soc. Cosmet. Chem., 34, pp. 215-225, (August, 1983), discloses that several cosmetics and, in particular, certain cosmetic emollients, caused follicular hyperkeratosis when applied to the external ear canal of rabbits. Their results showed that many common emollients were comedogenic, i.e., capable of causing the hyperkeratosis described above, and thus, would not be desirable for many cosmetic compositions due to the possibility of facilitating the formation of acne.

Compounds are classified as comedogenic or non-comedogenic based on their score in a comedogenicity test outlined by Klingman et al., Cosmetic Arch. Derm., Vol. 106, pp. 843-850, the content which is expressly incorporated herein by reference. In this test, non-comedogenic compounds score less than 1.5, out of a possible score of 5, while comedogenic compounds score above 1.5. The lowest values, of course, are preferred for non-comedogenic cosmetic formulations.

While the Morris article discloses a number of vegetable oils which have desirable non-comedogenic properties, these compounds are generally not desirable for use as cosmetic emollients. Vegetable oils are tri-ester (triglycerides) and do not provide the skin feel of mono or diesters. For example, isopropyl myristate is a mono-ester of myristic acid and isopropyl alcohol. This compound is comedogenic and has a light, desirable skin feel. Isopropyl myristate has been formulated into a wide number of cosmetic because of this desirable skin feel property, however, its comedogenic properties have been only recently discovered. As a result, formulators find this ingredient undesirable for most cosmetic formulations.

Applicants have now discovered a wide range of ricinoleic acid esters which are suitable for use as cosmetic emollients while providing non-comedogenicity to the overall cosmetic formulation.

SUMMARY OF INVENTION

This invention relates to a method for imparting non-comedogenicity to a cosmetic composition which comprises adding to a cosmetic composition a predetermined amount of an ester of ricinoleic acid to act as an emollient. The preferred ricinoleic acid esters have the formula:

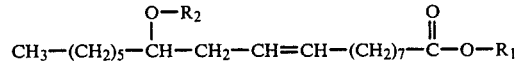

wherein:
$R_1$ is a straight or branched chain alkyl or alkenyl group having between one and 40 carbon atoms;
$R_2$ is hydrogen;

connected to a straight or branched chain alkyl or alkenyl group having between one and 40 carbon atoms; or between one and 40 moles ethylene or propylene oxide; and
the total molecular weight of $R_1$ and $R_2$ is at least about 150, preferably greater than about 170.

DETAILED DESCRIPTION OF THE PREFERRED EMBODIMENTS

A number of ricinoleate esters have been found to be suitable as cosmetic emollients which impart non-comedogenic properties to cosmetic formulations. These compounds include the mono esters or diesters or ricinoleic acid having a certain minimum molecular weight.

For example, cetyl ricinoleate was found to have a comedogenic score of 0.66, as shown in Table I, while cetyl acetyl ricinoleate was found to have a factor of 0.0 Applicants have found that other ricinoleates of lower molecular weight have higher scores and, accordingly, do not possess non-comedogenic properties. The following table summarizes the comedogenic score (i.e., the Klingman Factor) for certain compounds.

TABLE I

| Compound | Klingman Factor |
| --- | --- |
| cetyl acetyl ricinoleate | 0.0 |
| cetyl ricinoleate | 0.6 |
| butyl acetyl ricinoleate | 2.6 |
| isopropyl myrictate | 4.0 |

Applicants have discovered that by increasing the molecular weight of the esteriified substituents of ricinoleic acid, non-comedogenic compounds which are useful as cosmetic emollients can be obtained. The minimum molecular weight for $R_1$ and $R_2$ substituents which produce a non-comedogenic (i.e., less than 1.5) compound is about 150. However, it is preferred to select $R_1$ and $R_2$ so that the total molecular weight is at least about 170 and most preferably about 200 or higher.

There is no maximum on molecular weight for such compounds, although those having less than a total of about 80 to 120 carbon atoms (total of $R_1$ and $R_2$) are preferred.

The following examples illustrate typical formulations utilizing the emollients of the invention. it should be noted that depending upon the desired product and overall formulation, the amount of emollient can vary widely. Generally, they may account for from about 0.2 to 99 percent by weight. The higher proportions correspond to cosmetic compositions which are similar to petrolatums or mineral oils, while the lower range of proportions is used when these compounds are used as emollient or emulsifier additives. Typical additive amounts range from about 10 to 25 percent by weight of the overall composition.

While it is also possible to obtain non-comedogenic formulations by utilizing small amounts (i.e., generally less than about 5 to 10 weight percent) of comedogenic compounds, this usually does not result in an overall composition having the desired skin-feel characteristics. This is because the balance of the formulation will dilute the comedogenic compound to a low concentration. In addition, the formulations options are limited when comedogenic compounds must be diluted.

In comparison, the compounds of the invention can be used in any proportions, even as high as 99 to 100 weight percent, without any comedogenic effects upon the skin, while imparting the desired texture, smoothness and skin-feel characteristics in the product.

Applicants are not aware of any limitations as to the type of cosmetic preparation in which the emollients of the invention can be incorporated, or as to the quantity or proportion of emollient used. Thus, this invention should not be limited to the specific formulations disclosed herein.

EXAMPLES

The scope of the invention is further described in connection with the following examples which are set forth for the sole purpose of illustrating the preferred embodiments of the invention and which are not to be construed as limiting the scope of the invention in any manner. In these examples, all parts given are by weight unless otherwise specified.

EXAMPLE 1

Lipstick Formula

|  | Parts |
| --- | --- |
| Phase A - Base | |
| Castor Oil | 33.77 |
| Candelilla | 22.00 |
| Carnauba | 1.50 |
| Subtotal: | 57.27 |
| Phase B - Color Mix | |
| Yellow #5 C69-002 (35% in Castor Oil) | 8.25 |
| Blue #1 C39-4933 (35% in Castor Oil) | 0.77 |
| Red #7 C19-0717 (35% in Castor Oil) | 2.35 |
| TiO$_2$ A-420 (55% in Castor Oil) | 6.36 |
| Subtotal: | 17.73 |
| Phase C - Additive | |
| Cetyl acetyl ricinoleate | 25.00 |
| Total: | 100.00 |

EXAMPLE 2

Cationic Hand Lotion

| Ingredients | Parts |
| --- | --- |
| Phase A | |
| Water, Deionized | 74.15 |
| (1) 2% Methocel E4M Soln. | 10.00 |
| Phase B | |
| Propylene Glycol | 1.00 |
| Methylparaben | 0.25 |
| Propylparaben | 0.10 |
| Phase C | |
| (2) Arosurf TA-100 | 1.50 |
| Glyceryl hydroxystearate | 2.00 |
| Cetyl acetyl ricinoleate | 10.00 |
| (3) SF96-350 | 1.00 |
|  | 100.00 |

(1) Dow Chemical Company
(2) Sherex Chemical Company
(3) General Electric Company, Silicone Products Division Procedure Weigh and combine Phase A, begin gentle mixing with propeller agitation and heat to 80° C. Combine Phase B, mix well and heat to 40° C. Add Phase B to Phase A with gentle mixing. Combine phases C, heat to 80° C., and mix until clear and uniform. Add Phase C to Phase A and B when both phases are at 80° C. Maintain heat and agitation for ten minutes before cooling. Begin cooling and continue propeller agitation. Discontinue mixing at 30° C.

EXAMPLE 3

Hand Cream

| Ingredients | Parts |
| --- | --- |
| Phase A | |
| Water, Deionized | 70.65 |
| (1) 2% Carbopol 934 Soln. | 10.00 |
| Phase B | |
| Propylene Glycol | 3.00 |
| Methylparaben | 0.25 |
| Propylparaben | 0.10 |
| Triethanolamine 99.0% | 0.70 |
| (2) Hetoxol L-4 | 0.80 |
| Phase C | |
| (3) Emersol 132 | 1.50 |
| Cetyl acetyl ricinoleate | 10.00 |
| Glyceryl hydroxystearate | 2.00 |
| (4) 200 Fluid (350 CTS) | 1.00 |

(1) B. F. Goodrich Chemical Company
(2) Heterene Chemical Company
(3) Emery Industries, Inc.
(4) Dow Corning Corporation The procedure for this Example would be the same as that of Example 2.

The previous formulations are examples of non-comedogenic formulations due to the substitution of a completely non-comedogenic emollient (i.e. cetyl acetyl ricinoleate) for other, lower molecular weight mono or diester (comedogenic) compounds of the prior art.

EXAMPLE 4

Tanning Oil (Comparative Example)

| Isopropyl Myristate | 50.00 |
| --- | --- |
| Propylene Glycol | 50.00 |

| | |
|---|---|
| | 100.00% |

EXAMPLE 5

Tanning Oil

| | |
|---|---|
| Cetyl Acetyl Ricinoleate | 50.00 |
| Propylene Glycol | 50.00 |
| | 100.00% |

Procedure

Admix both ingredients at room temperature until uniform.

Example 4 Tanning Oil with isopropyl myristate is comedogenic with a test score between three and four and by substituting Cetyl Acetyl Ricinoleate for isopropyl myristate, Example 5, the Tanning Oil becomes non-comedogenic with a test score near zero.

While it is apparent that the invention herein disclosed is well calculated to fulfill the objects above state, it will be appreciated that numerous modifications and embodiments may be devised by those skilled in the art, and it is intended that the appended claims cover all such modifications and embodiments as fall within the true spirit and scope of the present invention.

We claim:

1. A method for imparting non-comedogenicity to a cosmetic composition which comprises incorporating into a cosmetic composition an effective non-comedogenic amount of an ester of ricinoleic acid to act as an emollient, said ricinoleic acid ester having the formula:

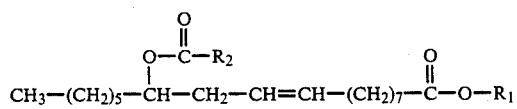

wherein:
$R_1$ is a straight or branched chain alkyl or alkenyl group having between one and 40 carbon atoms;
$R_2$ is a straight or branched chain alkyl or alkenyl group having between one and 40 carbon atoms; and
the total molecular weight of $R_1$ and $R_2$ is at least about 150.

2. A method for imparting non-comedogenicity to a cosmetic composition which comprises incorporating into a cosmetic composition an effective non-comedogenic amount of an ester of ricinoleic acid to act as an emollient, said ricinoleic acid ester having the formula:

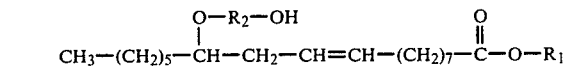

wherein:
$R_1$ is a straight or branched chain alkyl or alkenyl group having between one and 40 carbon atoms;
$R_2$ between one and 40 moles ethylene or propylene oxide;
the total molecular weight of $R_1$ and $R_2$ is at least about 150.

3. A method for imparting non-comedogenicity to a cosmetic composition which comprises incorporating into a cosmetic composition an effective non-comedogenic amount of an ester of ricinoleic acid to act as an emollient, said ricinoleic acid ester having the formula:

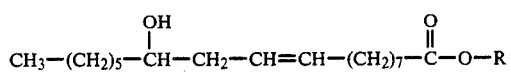

wherein: R is a straight or branched chain alkyl or alkenyl group having up to 15 carbon atoms and a total molecular weight of at least about 150.

4. A method for imparting non-comedogenicity to a cosmetic composition which comprises incorporating into a cosmetic composition an effective non-comedogenic amount of an ester of ricinoleic acid to act as an emollient, said ricinoleic acid ester having the formula:

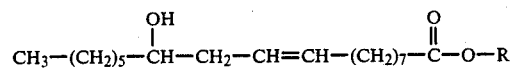

wherein: R is a straigt or branched chain $C_{16}$ alkenyl group or a branched chain $C_{16}$ alkyl group.

5. A method for imparting non-comedogenicity to a cosmetic composition which comprises incorporating into a cosmetic composition an effective non-comedogenic amount of an ester of ricinoleic acid to act as an emollient, said ricinoleic acid ester having the formula:

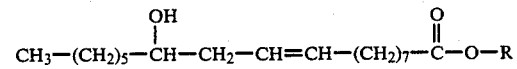

wherein: R is a straight or branched alkyl or alkenyl group of between 17 and 40 carbon atoms.

6. A method for imparting non-comedogenicity to a cosmetic composition which comprises adding to a cosmetic composition an effective non-comedogenic amount of cetyl acetyl ricinoleate to act as an emollient.

* * * * *